US010561965B2

(12) United States Patent
Kochergin et al.

(10) Patent No.: US 10,561,965 B2
(45) Date of Patent: Feb. 18, 2020

(54) FRACTAL FLOW DEVICES AND METHODS OF USE

(71) Applicant: Amalgamated Research LLC, Twin Falls, ID (US)

(72) Inventors: Vadim N. Kochergin, Twin Falls, ID (US); Michael M. Kearney, Twin Falls, ID (US)

(73) Assignee: Amalgamated Research LLC, Twin Falls, ID (US)

( * ) Notice: Subject to any disclaimer, the term of this patent is extended or adjusted under 35 U.S.C. 154(b) by 192 days.

(21) Appl. No.: 15/176,919

(22) Filed: Jun. 8, 2016

(65) Prior Publication Data
US 2017/0354903 A1    Dec. 14, 2017

(51) Int. Cl.
*B01D 15/36* (2006.01)
*C02F 1/28* (2006.01)
*C02F 1/00* (2006.01)
*B01D 15/18* (2006.01)
*C02F 1/42* (2006.01)
*C02F 1/72* (2006.01)

(52) U.S. Cl.
CPC ....... *B01D 15/361* (2013.01); *B01D 15/1842* (2013.01); *C02F 1/006* (2013.01); *C02F 1/28* (2013.01); *C02F 1/42* (2013.01); *C02F 1/725* (2013.01); *C02F 2001/422* (2013.01); *C02F 2001/425* (2013.01); *C02F 2301/028* (2013.01)

(58) Field of Classification Search
CPC ................... F15D 1/14; B01D 15/361; B01D 15/1864–1885; B01D 15/1821–1857; B01D 15/1842; B01D 15/22; C02F 1/42
See application file for complete search history.

(56) References Cited

U.S. PATENT DOCUMENTS

| | | | |
|---|---|---|---|
| 1,722,497 A | 7/1929 | Foster | |
| 4,636,315 A | 1/1987 | Allen, Jr. et al. | |
| 4,673,507 A | 6/1987 | Brown | |
| 5,626,750 A | 5/1997 | Chinn | |
| 6,616,327 B1 | 9/2003 | Kearney et al. | |
| 7,390,408 B2 | 6/2008 | Kearney et al. | |
| 8,512,560 B2 | 8/2013 | Paschedag et al. | |
| 2001/0032814 A1* | 10/2001 | Kearney | B01D 15/14 210/284 |
| 2004/0188337 A1 | 9/2004 | Miers, Jr. | |
| 2011/0168632 A1* | 7/2011 | Valery | B01D 15/18 210/659 |

(Continued)

FOREIGN PATENT DOCUMENTS

WO    2012/010620 A1    1/2012
WO    2015/023678 A1    2/2015

OTHER PUBLICATIONS

PCT International Search Report, PCT/US2017/023339, dated Jul. 13, 2017.

(Continued)

Primary Examiner — Liam Royce
(74) Attorney, Agent, or Firm — TraskBritt

(57) ABSTRACT

A fractal flow device comprising at least one fractal pack. The at least one fractal pack comprises at least two fractal cells, where each fractal cell comprises a fractal distributor, a chamber adjacent the fractal distributor, and a fractal collector adjacent the chamber. Methods of using the fractal flow device are also disclosed.

30 Claims, 7 Drawing Sheets

(56) References Cited

U.S. PATENT DOCUMENTS

2012/0097591 A1* 4/2012 Berthold ................ B01D 15/14
              210/198.3
2013/0068671 A1* 3/2013 Gebauer ............ B01D 15/1864
              210/85

OTHER PUBLICATIONS

PCT International Written Opinion, PCT/US2017/023339, dated Jul. 13, 2017.
Gongqiang He, Fractal distributor design and experiments, AICHE Spring Meeting, Mar. 30-Apr. 4, 2014, presentation.
He et al., CFD Simulation and Experimental Investigation of a Fractal Fluid Distributor, Canadian Chemical Engineering Conference, Oct. 2015, presentation.
European Extended Search Report and Opinion for European Application No. 17810657.1, dated Dec. 19, 2019, 7 pages.

* cited by examiner

FRACTAL FLOW DEVICES AND METHODS OF USE

TECHNICAL FIELD

Embodiments of the application relate generally to fractal flow devices and to methods of separating or purifying a component (or components) of a multicomponent fluid stream using the fractal flow devices. More particularly, embodiments of the disclosure relate to the fractal flow devices having at least one fractal pack that includes at least two fractal cells and to methods of using the fractal flow devices.

BACKGROUND

Fluid processes conventionally exhibit severe limits on operation due to bed pressure drop, kinetics, and flow uniformity. These limits are placed on, for example, productivity, process efficiency, energy use, system size, environmental compatibility, and capital/operating costs. As one example of how these limits occur, the flow rate through a bed may be constrained because as flow rate increases, bed pressure drop increases. The pressure drop may reach a point where the pressure rating of a column containing the bed may be exceeded, the bed may begin to unacceptably compress, bed particles may be destroyed, and excessive energy may be required for operation. Clearly, this effect places limits on productivity (limits on flow rate) and design and cost (higher pressure requires additional structural strength). As another example, high linear velocities can result in unacceptably poor interaction or reaction of a fluid with the bed material. That is, the kinetic requirements of the system are self-limiting. An excessively high linear velocity of a fluid through a bed will result in an insufficient contact time of the fluid with the bed particles. Clearly, this places limits on productivity (again, flow rate is limited).

Spreading out a bed to a wide (large cross section) or shallow (shallow depth or short travel path) geometry instead of a high (long travel path), narrow (relatively small cross section transverse to the direction of flow) geometry will reduce both the bed pressure drop and the linear velocity of a fluid passing through the bed. While both of these effects would be very beneficial, such column construction is not prevalent because of the difficulty of distributing and collecting fluid across a wide, shallow bed (a large cross section). Any inhomogeneity or turbulence in the fluid introduced into the column cannot normally be attenuated through a wide, shallow bed so the inhomogeneities are reflected as inefficiencies and unacceptable processing. For example, in chromatography, such problems result in band broadening and poor separation of the components of a feed mixture.

A fluid treatment apparatus is disclosed in U.S. Pat. No. 4,673,507 to Brown, the contents of which are incorporated herein by this reference. The fluid treatment apparatus can be used for shallow bed operation. However this fluid treatment apparatus lacks significantly distributed fluid feed and collection systems and is dependent upon maintaining the bed in an overpacked condition where the particles are confined within the resin bed so that they are subjected to compression at all times. A substantially uniform fluid flow distribution across the bed is achieved by employing resins of fine (substantially uniform) particle size, which are maintained in the overpacked condition. This fluid treatment apparatus restricts process fluid flow across the bed.

U.S. Pat. No. 5,626,750 to Chinn, the contents of which are incorporated herein by this reference, discloses an apparatus for treating a fluid. In this apparatus, first and second "particle free cavities" are provided above and below a retained particle bed. Even flow of fluid through the retained particle bed is provided simply by the pressure drop across the retained particle bed, which is a function of the pressures in the first and second cavities. No provision is made to substantially control fluid flow characteristics (eddies, or turbulent zones) in process fluid streams near the surface of the retained particle bed.

U.S. Pat. No. 7,390,408 to Kearney, the contents of which are incorporated herein by this reference, solves the above problems using a shallow bed with distributors and collectors designed using fractal geometry. This type of vessel has become successful in industrial implementation and there are several benefits to this vessel design. For example, distribution and collection of fluids is extremely uniform. Because of the uniformity, very shallow beds of processing medium can be used without problems with channeling or non-coverage of the processing media. Pressure drop is subsequently very low, which means that the vessels using this technology can be rated for lower pressures than conventional devices. Heads of the shallow bed vessels are substantially flat plates in contrast to the spherical or dished heads of most conventional pressure vessels. In order to increase the capacity of the shallow bed vessels, their diameter must be increased, which leads to increased pressures on the heads. As the diameter increases, the pressure on the heads increases proportionally and mechanical support of the heads must be increased. The increased diameter increases the size and weight as the shallow bed vessels are constructed for higher capacity and higher throughput uses. The larger size also increases the amount of space occupied by the shallow bed vessels, making the shallow bed vessels more difficult to handle.

Filter presses have been used for more than 100 years to remove solids from a slurry or suspension. The filter press includes multiple filtration plates, each having a cloth filter and a chamber through which the slurry is passed. The slurry enters each of the filtration plates through a single port and the solids accumulate on the cloth filter as the liquid of the slurry passes through the filtration plates. The filtration plates have small holes for collecting the filtered liquid as the filtered liquid exits the filter press. Various methods of compressing and removing the solids (i.e., the filter cake) from the cloth filter have been developed. Following moisture removal, the filter cake is removed from the filter press by separating the filtration plates from one another and allowing the solids to drop out of the filter press by gravity. Uniform flow of the slurry through the filtration plates is not required because the solids are removed by filtration through the cloth filter.

BRIEF SUMMARY

Disclosed is a fractal flow device that comprises at least one fractal pack. The at least one fractal pack comprises at least two fractal cells, where each fractal cell comprises a fractal distributor, a chamber adjacent the fractal distributor, and a fractal collector adjacent the chamber.

Also disclosed is a method of using a fractal flow device. The method comprises introducing a fluid stream to a fractal flow device, flowing the fluid stream through at least one fractal pack, and separating at least one component from the fluid stream to produce a product stream. The fractal flow device comprises at least one fractal pack comprising at least two fractal cells, where each fractal cell comprises a fractal distributor, a chamber adjacent the fractal distributor, and a fractal collector adjacent the chamber.

DETAILED DESCRIPTION

A fractal flow device having at least one fractal pack is disclosed. The fractal pack provides increased capacity to the fractal flow device without increasing pressure within the fractal flow device during its use and operation. The increased capacity is achieved without substantially increasing the size or weight of the fractal flow device. The fractal flow device is, thus, compact and there is no increase in volume (i.e., equipment footprint) occupied by the fractal flow device. The fractal flow device may include a single fractal pack or multiple fractal packs that are configured in parallel or in series depending on the desired application of the fractal flow device. The fractal pack includes fractal cells that are configured in parallel or series depending on the desired application of the fractal flow device. The fractal flow device is used to separate a component(s) of a multi-component fluid stream.

As used herein, the term "fractal" means and includes a pattern (i.e., shape or geometry) that can be repeatedly divided into small parts or repeatedly multiplied into larger parts that are the same or similar to the original pattern (i.e., shape or geometry). The fractal flow device of the disclosure includes at least one component having a fractal pattern, such as one or more of a fractal plate, a fractal distributor, a fractal collector, a fractal cell, or a fractal pack.

Figure 1:
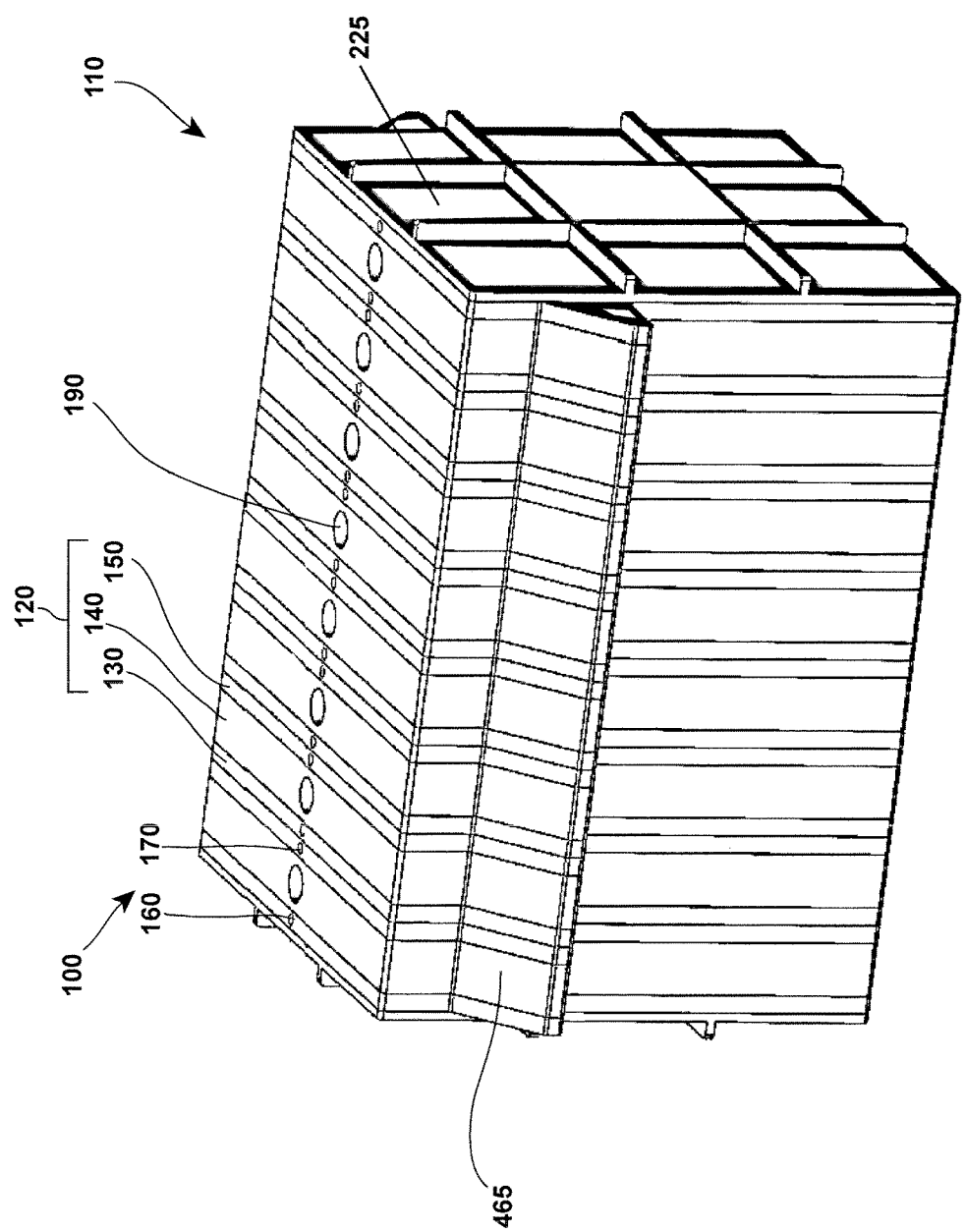
FIG. 1 is a schematic representation of a fractal pack according to embodiments hereof.

As shown in FIG. 1, an embodiment of the fractal flow device 100 includes a fractal pack 110 having multiple fractal cells 120, such as at least two fractal cells 120. While the fractal flow device 100 illustrated in FIG. 1 includes eight fractal cells 120, the fractal pack 110 may include fewer or more fractal cells 120. The fractal cells 120 may be configured in series or parallel, depending on the desired application for the fractal flow device 100. Each of the fractal cells 120 includes a fractal distributor 130, a chamber 140, and a fractal collector 150. The fractal distributor 130 has a fractal cell inlet 160 through which the fluid stream enters the fractal flow device 100 and the fractal collector 150 has a fractal cell outlet 170 through which the fluid stream exits the fractal flow device 100. The fractal distributors 130, chambers 140, and fractal collectors 150 enable the fractal pack 110 to achieve desired separation of the fluid stream, with the fractal distributors 130 and fractal collectors 150 providing uniform distribution of the fluid stream into a fluid processing medium (not shown) in the chamber 140.

Figure 2:
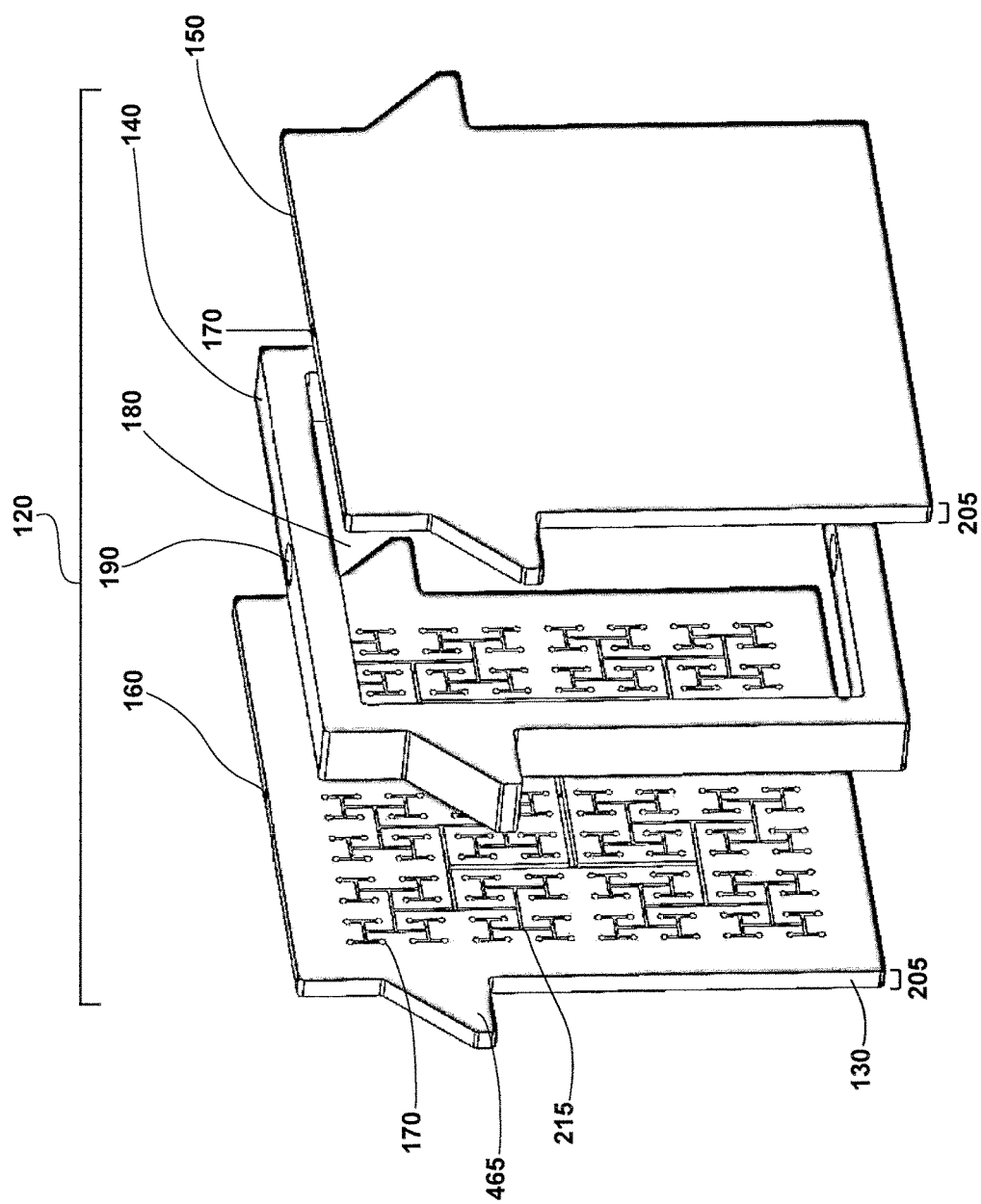
FIG. 2 is a schematic representation of a fractal cell according to embodiments hereof.

As shown in FIG. 2 and described in more detail below, each of the fractal distributor 130 and the fractal collector 150 includes fractal plates 205 having a fractal pattern 215 that provides progressively increasing scale or progressively decreasing scale flow paths. The fractal cells 120 may be positioned horizontally adjacent (i.e., in the x direction) to one another, as illustrated in FIG. 1, or vertically adjacent (i.e., in the y direction) to one another (not shown), to form the fractal pack 110. The fractal cells 120 may directly contact one another and, optionally, may be contained by a fastening element 225, such as by end plates, a support head, a hydraulic press, a hydraulic jack, bolts, or other fastening element. The fastening element 225 provides mechanical strength to the fractal cells 120 during use and operation of the fractal flow device 100, maintaining the fractal cells 120 in contact with one another and in place as the fractal cells 120 are subjected to operation and pressure changes. The fastening element 225 may enable the fractal flow device 100 to be operated at relatively high pressures while maintaining fluid communication between the fractal cells 120. By way of example only, the fastening element 225 may include end plates positioned on opposing ends of the fractal pack 110, as shown in FIG. 1. The end plates may be adjusted to maintain pressure on the fractal cells 120, bringing the fractal cells 120 into contact with one another and enabling fluid communication between the fractal cells 120. Alternatively, the fastening element 225 may include bolts and nuts (not shown) that pass through appropriately-aligned holes (not shown) in portions of the fractal cells 120 not occupied by the fractal pattern 215. The fastening element 225 may alternatively include a hydraulic jack (not shown) secured to opposing ends of the fractal pack 110.

As shown in FIG. 2, the fractal cell 120 includes the fractal distributor 130, the chamber 140, and the fractal collector 150. The fractal distributor 130 of each fractal cell 120 is configured to flow (i.e., distribute) the fluid stream into the chamber 140, and the fractal collector 150 of each fractal cell 120 is configured to collect the fluid stream after the fluid stream passes through the chamber 140. The fractal distributor 130 uniformly distributes the fluid stream into the chamber 140 in a recursive flow path arranged in the fractal pattern 215. The fractal collector 150 merges the fluid streams exiting the chamber 140 into a single fluid stream that exits the fractal flow device 100. For simplicity, connector elements that provide fluid communication between the fractal cells 120 of the fractal pack 110 or that provide fluid communication into and out of the fractal pack 110 or between fractal packs 110 are not shown in FIGS. 1 and 2. However, the connector elements are described in more detail below.

Figure 3:
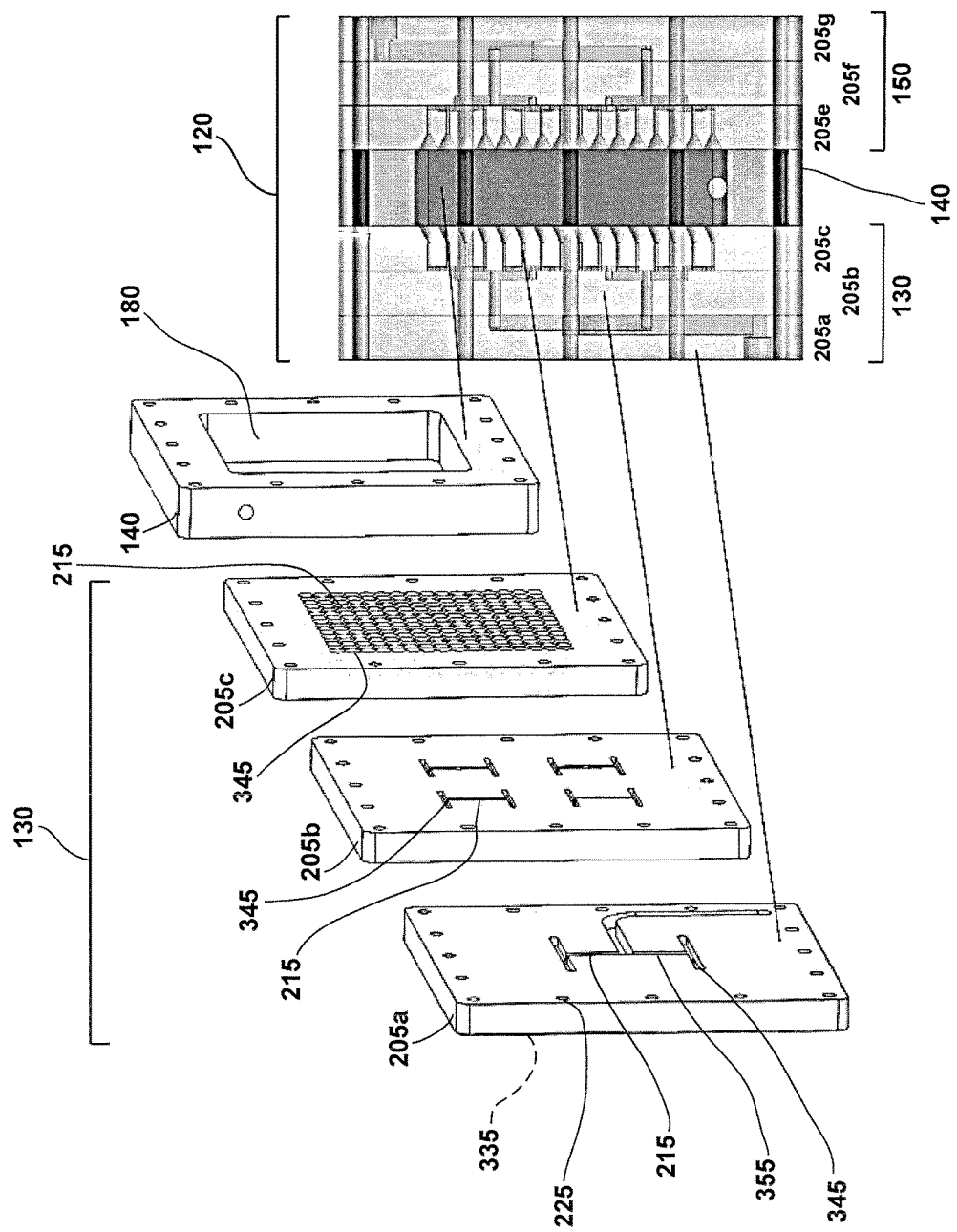
FIG. 3 is a schematic representation of a fractal cell according to embodiments hereof.

The fractal distributor 130 includes one or more fractal plates 205. For simplicity, the fractal plates are referred to herein as fractal plate 205 or fractal plates 205, while specific fractal plates are referred to herein as fractal plates 205a, 205b, 205c, etc. As shown in FIG. 3, the fractal distributor 130 includes three fractal plates 205a, 205b, 205c. However, the fractal distributor 130 may include more or fewer fractal plates 205 depending on the desired separation of the fluid stream. The fractal plates 205 of the fractal distributor 130 include fractal plate inlets 335, fractal plate outlets 345, and channels 355 through which the fluid stream flows. The fractal plate inlets 335, fractal plate outlets 345, and channels 355 form the flow path that is arranged in the fractal pattern 215. The channels 355 distribute the fluid stream between the fractal plate inlets 335 and the fractal plate outlets 345 before the fluid stream exits the fractal distributor 130. The fractal pattern 215 on one of the fractal plates, such as fractal plate 205a, has the same or a similar geometric arrangement as the fractal pattern on another fractal plate, such as fractal plates 205b, 205c, except that the fractal pattern 215 on each subsequent fractal plate (i.e., fractal plates 205b, 205c) has a progressively decreasing scale relative to that of fractal plate 205a. By way of example only, the fractal pattern 215 may be an H-shape, as illustrated in FIGS. 2 and 3. However, other fractal patterns 215, such as a T-shape, Y-shape, or a three-dimensional shape, may be used. The fractal pattern 215 may include, but is not limited to, one of the fractal patterns described in U.S. Pat. No. 6,616,327 to Kearney et al. and U.S. Pat. No. 7,390,408 to Kearney et al., the entire disclosure of each of which is hereby incorporated by reference herein in its entirety.

The fractal plates 205 of the fractal distributor 130 are aligned with one another so that the fluid stream passes into the fractal plate inlet(s) 335, through the channel(s) 355, and exits the fractal plate outlet(s) 345 of the fractal plate 205 before passing into the fractal plate inlet(s) 335, through the channel(s) 355, and exits the fractal plate outlet(s) 345 of the next fractal plate 205. The fractal distributor 130 may be configured and formed as described in U.S. Pat. No. 6,616,327 to Kearney et al. and U.S. Pat. No. 7,390,408 to Kearney et al. The fractal plates 205 of the fractal distributor 130 may be positioned adjacent to one another such that fractal distribution from large to progressively smaller scales occurs as the fluid stream passes through the fractal distributor 130. By including one or more fractal plates 205 having the same fractal pattern 215, the fractal distributor 130 has a relatively small width (i.e., thickness) relative to its length or height. The height to width ratio of the fractal plates 205 may range from about 2:1 to about 20:1 or greater.

The fractal distributor 130 may include an outlet density sufficient to provide reduced turbulence or internal mixing of the fluid stream as the fluid stream passes into the chamber 140. The outlet density may be increased as desired by recursively multiplying the fractal pattern 215 on a smaller and smaller scale. As used herein, the term "outlet density" means and includes the number of outlets in the unit cross-sectional area of the fractal plate 205 directly adjacent to the chamber 140. By way of example only, the fractal distributor 130 may have an outlet density of greater than or equal to approximately 64 outlets/ft$^2$, such as greater than or equal to approximately 100 outlets/ft$^2$, greater than or equal to approximately 200 outlets/ft$^2$, greater than or equal to approximately 500 outlets/ft$^2$, or greater than or equal to approximately 1024 outlets/ft$^2$. The greater the outlet density of the fractal plate 205 directly adjacent to the chamber 140, the more uniform distribution of the fluid stream into the chamber 140.

As illustrated in FIGS. 2 and 3, the fractal plates 205 are substantially square or rectangular in shape to enable efficient packing of the fractal pattern 215 on the fractal plates 205. However, circular or other shapes of the fractal plates 205 may be used depending on the desired efficiency of the fractal flow device 100 and its intended use.

Figure 4:
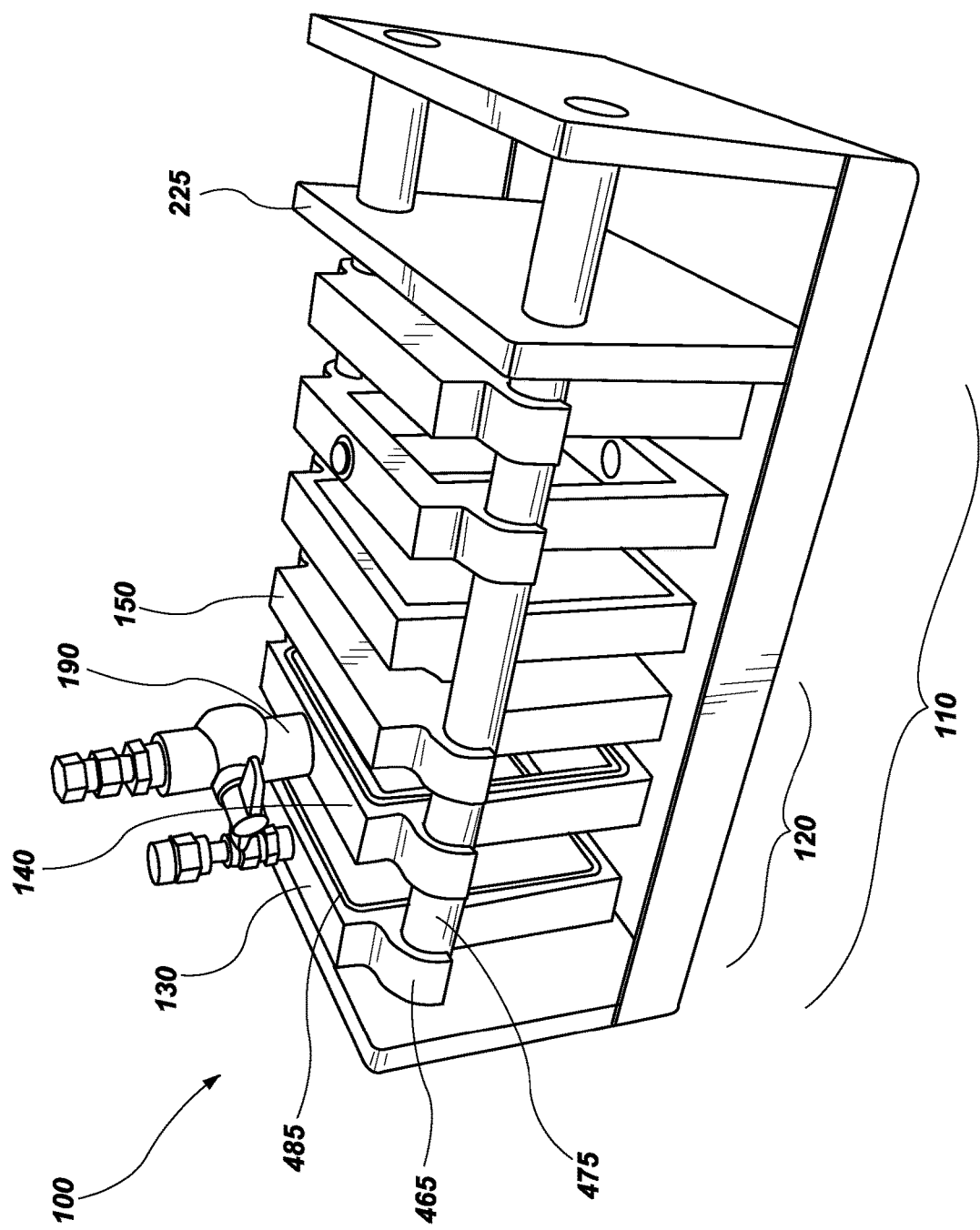
FIG. 4 is a photograph of a fractal flow device, according to embodiments hereof, including two fractal packs.

The chamber 140 of the fractal cell 120 includes an opening 180 for containing a fluid processing medium (not shown), such as an ion exchange resin or other separation medium, an adsorption medium, an absorption medium, a catalyst medium, or a reactive medium. As shown in FIG. 4, the chamber 140 may include a port 190 (see, also, FIGS. 1 and 2) through which the fluid processing medium is loaded. The fluid processing medium may be contained in the chamber 140 by a screen or filter cloth (not shown). The fluid processing medium may be selected depending on the components of the fluid stream and the intended application for the fractal flow device 100. The fluid processing medium in each of the fractal cells 120 of a particular fractal pack 110 may be the same or different. For instance, a cation exchange resin may be used in one fractal cell 120 and an anion exchange resin may be used in another fractal cell. Additionally, in situations where multiple fractal packs 110 are used, the fluid processing medium in each of the fractal packs 110 may be the same or different or that in each of the fractal cells 120 of the fractal packs 110 may be the same or different. For instance, a cation exchange resin may be used in the fractal cells 120 of one fractal pack 110 and an anion exchange resin may be used in the fractal cells 120 of another fractal pack 110. Upon exiting the fractal distributor 130, the fluid stream enters into and passes through the chamber 140 for separation. The opening 180 in the chamber 140 has a relatively small width (i.e., thickness) relative to its length or height. Only a small amount of fluid processing medium may be used in each chamber 140 since multiple fractal cells 120 are present in the fractal flow device 100. Thus, fluid processing media that are too expensive to be used in conventional equipment may be used in the fractal flow device 100 according to embodiments hereof. Additionally, the small amount of fluid processing medium used results in a reduced pressure drop across the chamber 140. Thus, very small size particles of the fluid processing medium may be used. Therefore, faster separation or reaction rates may be achieved because the fluid processing medium has a high surface area per unit volume.

The fractal collector 150 of the fractal cell 120 also includes one or more fractal plates 205. While the embodiment of the fractal collector 150 in FIG. 3 includes three fractal plates 205e, 205f, 205g, the fractal collector 150 may include more or fewer fractal plates 205 depending on the desired separation of the fluid stream. The fractal plates 205 of the fractal collector 150 also include fractal plate inlets 335, fractal plate outlets 345, and channels 355 through which the fluid stream flows. The fractal plate inlets 335, fractal plate outlets 345, and channels 355 form the flow path that is arranged in the fractal pattern 215. The channels 355 distribute the fluid stream between the fractal plate inlets 335 and the fractal plate outlets 345 before the fluid stream exits the fractal collector 150. Similar to the fractal pattern 215 on the fractal plates 205 of the fractal distributor 130, the fractal pattern 215 on one of the fractal plates 205 of the fractal collector 150, such as fractal plate 205e, has the same or a similar geometric arrangement as the fractal pattern on another fractal plate, such as fractal plates 205f, 205g, except that the fractal pattern 215 of each subsequent fractal plate (i.e., fractal plates 205f, 205g) has a progressively increasing scale relative to that of fractal plate 205e.

In one embodiment, the fractal collector 150 has the same number of fractal plates 205 as the fractal distributor 130. The fractal pattern 215 on the fractal plates 205 of the fractal collector 150 is also substantially similar to the fractal pattern 215 on the fractal plates 205 of the fractal distributor 130. However, the order in which the fractal plates 205 of the fractal collector 150 are configured is reversed such that the fractal plate 205 having the greatest number of fractal plate inlets 335 is directly adjacent to the chamber 140. In other words, the last fractal plate 205 of the fractal collector 150 (i.e., the fractal plate 205g, which is distal to the chamber 140) has the lowest outlet density. The outlet density may be decreased as desired by recursively dividing the fractal pattern 215 on a larger and larger scale. The fractal plates 205 of the fractal collector 150 may be positioned adjacent to one another such that fractal distribution from small to progressively larger scales occurs as the fluid stream passes through the fractal collector 150.

By way of example only and as shown in FIG. 3, a first fractal plate 205a of the fractal distributor 130 includes a single fractal plate inlet (not shown) and an H-shaped channel 355 having four fractal plate outlets 345. A second fractal plate 205b of the fractal distributor 130 is adjacent to the first fractal plate 205 and includes four inlets (not shown) and sixteen fractal plate outlets 345 with four H-shaped channels 355. A third fractal plate 205c of the fractal distributor 130 is adjacent to the second fractal plate 205b and includes sixteen inlets (not shown) and two hundred fifty-six fractal plate outlets 345 with sixteen H-shaped channels. The fractal plates 205a, 205b, 205c are aligned so that the fluid stream passes therethrough, from fractal plate outlets 345 of the first fractal plate 205a to fractal plate inlets 335 of the second fractal plate 205b, from fractal plate outlets 345 of the second fractal plate 205b to fractal plate inlets 335 of the third fractal plate 205c, and from fractal plate outlets 345 of the third fractal plate 205c to the chamber 140. While three fractal plates 205 are shown in FIG. 3, more or fewer fractal plates 205 may be present depending on the intended application. The chamber 140 is adjacent the third fractal plate 205c of the fractal distributor 130. The fractal collector 150 may include the same number of fractal plates 205 as the fractal distributor 130. The fractal plates 205e, 205f, 205g of the fractal collector 150 may include the same fractal pattern 215 as those of the fractal distributor 130, except that the order of fractal plates 205 is configured in a reverse direction. In other words, the fractal pattern 215 on fractal plates 205e, 205f, 205g corresponds to the fractal pattern 215 on fractal plates 205c, 205b, 205a, respectively. For instance, a fifth fractal plate 205e of the fractal distributor 130 adjacent to the chamber 140 may include two hundred fifty-six fractal plate inlets (not shown) and sixteen fractal plate outlets (not shown) with sixteen H-shaped channels (not shown), a sixth fractal plate 205f adjacent to the fifth fractal plate 205e may include sixteen inlets (not shown) and four outlets (not shown) with four H-shaped channels (not shown), and a seventh fractal plate 205g adjacent to the sixth fractal plate 205f may include four inlets (not shown) and one outlet (not shown) with one H-shaped channel (not shown). The fifth, sixth, and seventh fractal plates 205e, 205f, 205g of the fractal collector 150 are aligned so that the fluid stream passes therethrough, from fractal plate outlets of the fifth fractal plate 205e to fractal plate inlets of the sixth fractal plate 205f, from fractal plate outlets of the sixth fractal plate 205f to fractal plate inlets of the seventh fractal plate 205g, and exiting from the fractal plate outlets of the seventh fractal plate 205g. The fluid stream merges from the multiple fractal plate outlets of the fifth and sixth fractal plates 205e, 205f to a single outlet of the seventh fractal plate 205g.

Shoulders 465 on side surfaces of the fractal plates 205 of the fractal distributor 130, chamber 140, and the fractal plates 205 of the fractal collector 150 may be used to position the fractal cells 120 adjacent to one another, as shown in FIGS. 1, 2, and 4. For instance and as shown in FIG. 4, the fractal cells 120 may be positioned horizontally adjacent to one another by engaging the shoulders 465 on support structures 475, which are oriented substantially perpendicular to the fractal cells 120. The fractal distributors 130, chambers 140, and fractal collectors 150 may be positioned on the support structures 475 and maintained in direct contact with one another by the fastening element 225 to enable fluid communication between the fractal cells 120 during use and operation of the fractal flow device 100. For convenience in illustrating additional components, the fractal distributors 130, chambers 140, and fractal collectors 150 are shown in a spaced apart configuration in FIG. 4. The fractal distributor 130, the chamber 140, and the fractal collector 150 may, optionally, be separated from one another by a sealing element(s) 485, such as a gasket. The sealing element 485 may prevent the fluid stream from leaking between the fractal distributor 130, the chamber 140, and the fractal collector 150 during use and operation of the fractal flow device 100.

The fractal plates 205 of the fractal distributor 130 and fractal collector 150 may be formed from any compatible material onto which the fractal pattern 215 is to be formed. The material may also be compatible with the components of the fluid stream. For instance, the material, such as a plastic material or a metal material, may be resistant to corrosive, acidic, or basic components in the fluid stream. The plastic material may include, but is not limited to, polypropylene, polymethyl methacrylate (PMMA), polytetrafluoroethylene, and the metal material may include, but is not limited to, stainless steel. Since the fractal flow device 100 may be operated at a lower pressure than conventional equipment, the material of the fractal distributor 130 and the fractal collector 150 may be selected from materials not used in the conventional equipment due to this reduced structural requirement. The chamber 140 may be formed from the same or a similar material. The material of the fractal distributor 130, the chamber 140, and the fractal collector 150 may also be compatible with operating temperatures at which the fractal flow device 100 is utilized, such as from room temperature (from about 20° C. to about 25° C.) to about 85° C. The material of the fractal distributor 130, the chamber 140, and the fractal collector 150 may also be compatible with operating pressures at which the fractal flow device 100 is utilized, such as less than or equal to about 4 bar (less than or equal to about 400 kPa). By way of example only, the fractal distributor 130, chamber 140, and fractal collector 150 may be formed of PMMA.

The dimensions of the fractal plates 205 of the fractal distributor 130 and fractal collector 150 and of the chamber 140 may be selected depending on the desired capacity of the fractal flow device 100. By way of example only, each of the length and height of the fractal plates 205 and chamber 140 may independently range from approximately 2 inches to approximately 48 inches. The thickness (i.e., width) of the fractal plates 205 may range from approximately 0.1 inch to approximately 3 inches. The thickness (i.e., width) of the chamber 140 may be larger to accommodate the fluid processing medium, such as from approximately 0.2 inch to approximately 6 inches. In one embodiment, the fractal plates 205 are a 12.25-inch square and 1 inch thick. The chamber 140 is a 12.25-inch square and 2 inches thick.

The fractal flow device 100 also includes connector elements, such as tubing, piping, openings, etc., that provide fluid communication between the components of the fractal flow device 100. For instance, the fluid stream may pass between the fractal plate inlets 335, channels 355, and fractal plate outlets 345 of the fractal cells 120 and the chamber 140, which are located within (i.e., internally) the fractal cells 120. The fluid stream may pass from the fractal distributor 130, through the chamber 140, and into the fractal collector 150 by tubing or openings within the fractal cells 120. Alternatively, the fluid stream may pass between the components of the fractal cells 120 through externally located tubing (not shown). Thus, the fractal cells 120 of the fractal pack 110 may be in fluid communication through external connector elements or internal connector elements. The fractal flow device 100 also includes connector elements that introduce the fluid stream into the fractal flow device 100 and collect the fluid stream as the fluid stream exits the fractal flow device 100. While not illustrated in the drawings, a simple configuration of connector elements may be used in which tubing is connected to the fractal cell inlets 160 and fractal cell outlets 170 of each of the fractal cells 120 of FIGS. 1 or 2. The tubing may introduce the fluid stream into the fractal cells 120 and collect the fluid stream as the fluid stream exits the fractal cells 120. The fractal flow device 100 also includes valves, pumps, feed tanks, filters, pressure regulators, metering equipment, flow control equipment, and microprocessor equipment to distribute the fluid stream between the components of the fractal flow device 100. These elements of the fractal flow device 100 are well known in the art and are not described in detail herein.

Figure 5:
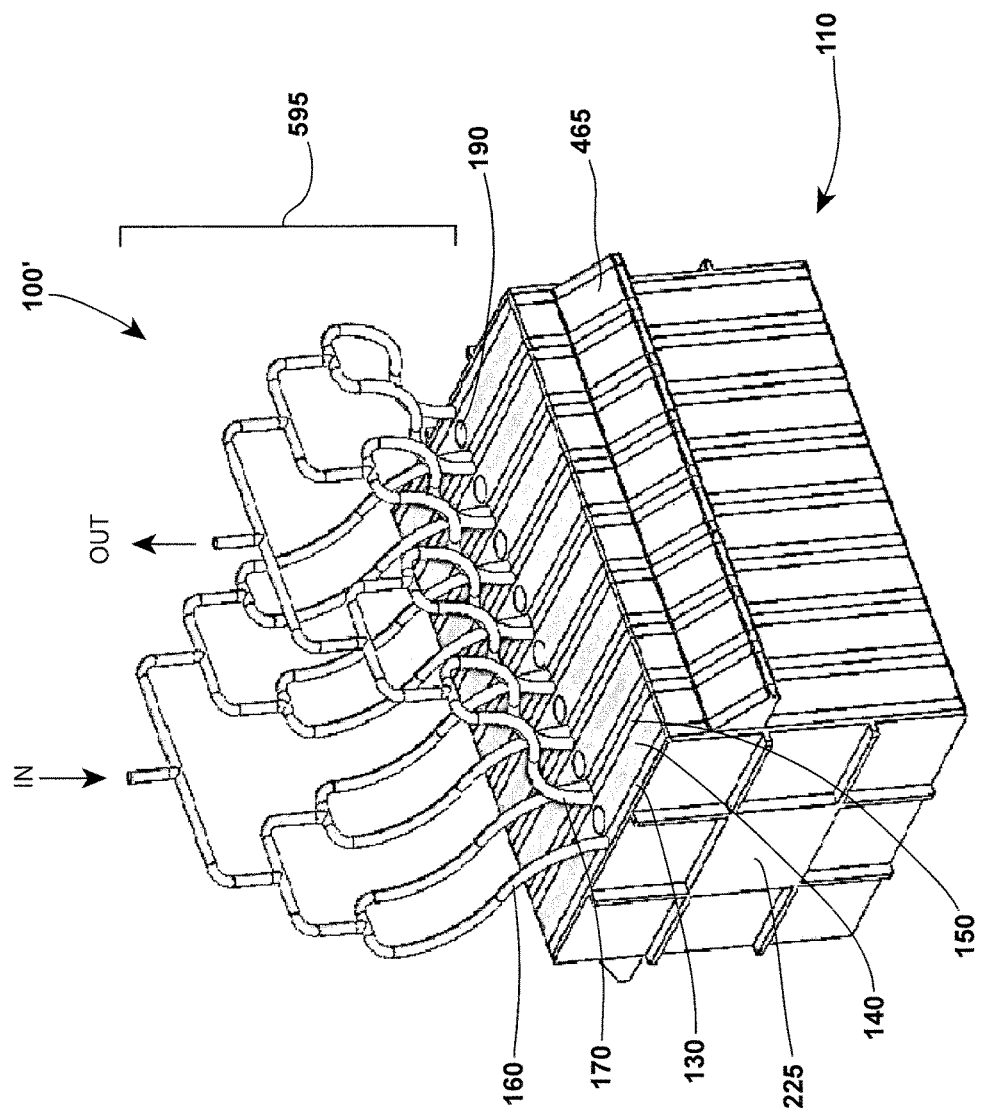
FIG. 5 is a schematic illustration of a fractal flow device, according to embodiments hereof, including a fractal pack and connector elements.
Figure 6:
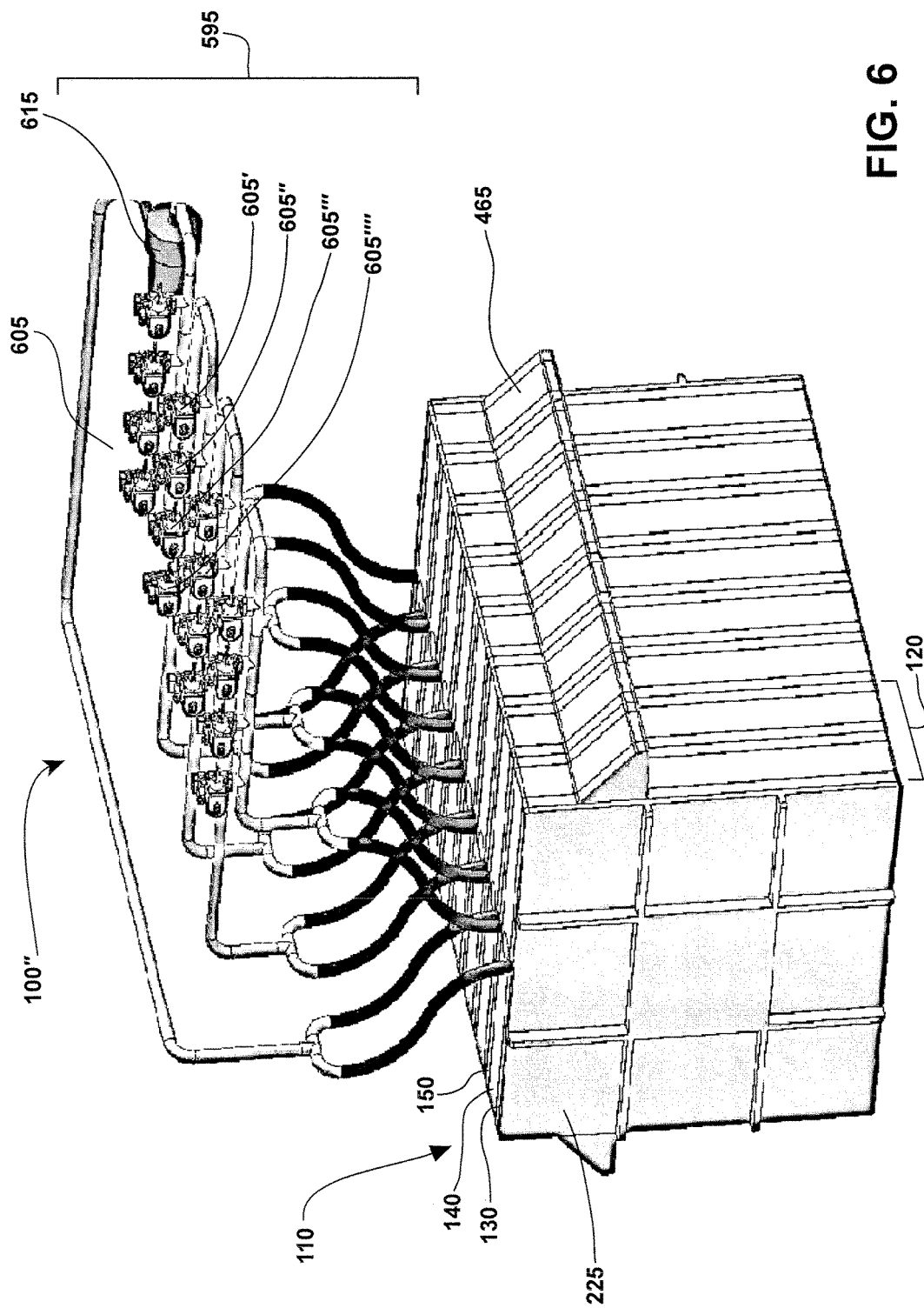
FIG. 6 is a schematic illustration of a fractal flow device, according to embodiments hereof, including a fractal pack and connector elements configured in an SMB operation.
Figure 7:
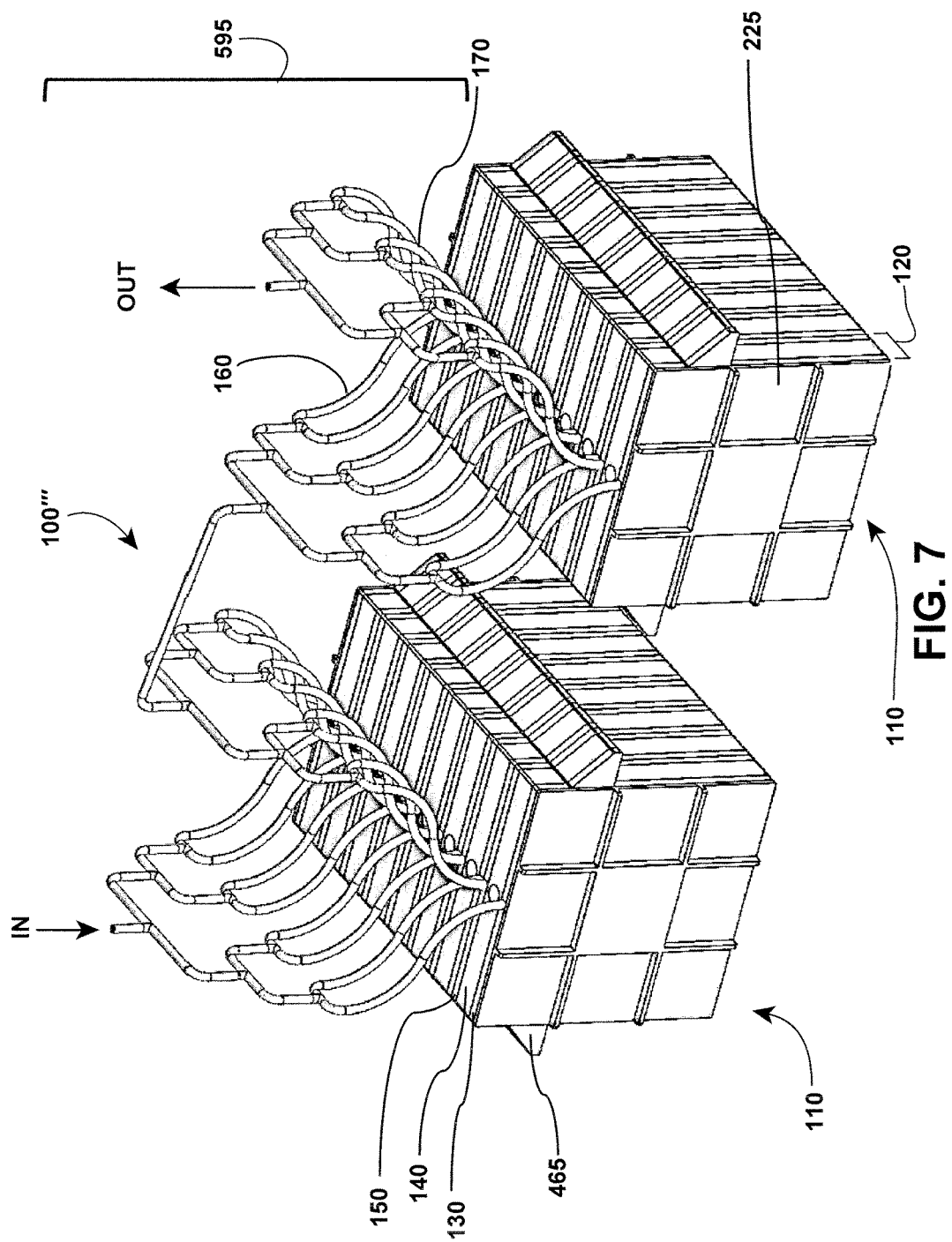
FIG. 7 is a schematic illustration of a fractal flow device, according to embodiments hereof, including two fractal packs and connector elements.

Connector elements that are located external to the fractal pack 110 may also be used in more complex embodiments of the fractal flow device 100. The connector elements may distribute the fluid stream through a single fractal pack 110 (see FIGS. 5 and 6) or through multiple fractal packs 110 (see FIG. 7). While FIGS. 5-7 illustrate fractal packs 110 having eight fractal cells 120, the fractal packs 110 may include fewer or greater numbers of fractal cells 120. The multiple fractal packs 110 may be configured for series operation, parallel operation, primary/secondary series operation, simulated moving bed operation, or carousel-type fluid operation depending on the desired application.

In embodiment of the fractal flow device 100' illustrated in FIG. 5, a fractal predistributor is used as a connector element 595 to distribute the fluid stream to the fractal pack 110. The fractal predistributor includes tubing that is itself configured in a fractal pattern, in addition to the fractal patterns 215 (see FIG. 2) present in the fractal distributors 130 and fractal collectors 150 of the fractal cells 120. The fractal predistributor provides an optimal equivalent flow rate of the fluid stream to each fractal cell 120. Upon passing through the fractal predistributor, the fluid stream is distributed (i.e., divided) into portions that enter the fractal distributors 130 of each of the fractal cells 120. The portions of the fluid stream then pass through the fluid processing medium in the chambers 140 and into the fractal collectors 150 before exiting the fractal cells 120. The portions of the fluid streams exiting the fractal collectors 150 are combined into a single feed stream and collected.

In yet another embodiment and as illustrated in FIG. 6, the fractal flow device 100" is configured for operation as a simulated moving bed (SMB). In the SMB configuration, one fractal cell 120 includes two fractal distributors 130, two chambers 140, and two fractal collectors 150. Tubing may be used as the connector elements 595 in combination with a valve arrangement 605 to distribute the fluid stream through the fractal pack 110. The valve arrangement 605 includes four valves for each fractal cell 120, a fluid stream valve 605', a water valve 605", an extract valve 605'", and a raffinate valve 605"". A pump 615, such as a recycle pump, may be used to flow the fluid stream through the fractal flow device 100". Additional components, such as feed tanks, filters, pressure regulators, metering equipment, flow control equipment, and microprocessor equipment may also be present to distribute the fluid stream through the fractal flow device 100". The fractal flow device 100" has two parallel inputs and two parallel outputs so that the fluid stream enters and exits the fractal cell 120 (including the two fractal distributors 130, two chambers 140, and two fractal collectors 150) in parallel.

In yet another embodiment and as illustrated in FIG. 7, the fractal flow device 100'" may include multiple fractal packs 110 and the connector elements 595, such as tubing. At least two fractal packs 110 may be in fluid communication with one another through the tubing. As shown in FIG. 7, two fractal packs 110, each having eight fractal cells 120, are in fluid communication with one another by tubing external to the fractal packs 110. However, the fractal flow device 100'" may include more than two fractal packs 110, each having more or less fractal cells 120. As illustrated in FIG. 7, the fractal cells 120 of each of the fractal packs 110 are configured in parallel while the two fractal packs 110 are configured in series. In other embodiments, it is contemplated that the connector elements 595 may be internal (not shown) to the fractal packs 110. It is also contemplated that the two fractal packs 110 may be configured in parallel (not shown).

The fractal flow devices 100, 100', 100", 100'" according to the embodiments hereof may be used to separate or purify a component from a multicomponent fluid stream. For instance, the fractal flow devices 100, 100', 100", 100'" may be used to decolorize or otherwise purify a fluid stream containing multiple components. Alternatively, the fractal flow devices 100, 100', 100", 100'" may be used to demineralize a fluid stream containing multiple components. By way of example only, the fractal flow devices 100, 100', 100", 100'" may be used in the water treatment, food and sweeteners, chemicals, biomass, renewables, pharmaceutical, mining, or petroleum industries.

During use and operation of the fractal flow devices 100, 100', 100", 100'" according to the embodiments hereof, the fluid stream enters the fractal plates 205 of the fractal distributor 130 of a first fractal cell and is distributed into multiple fluid streams. The fluid streams are uniformly distributed into the fluid processing medium of the chamber 140 of the first fractal cell 120. As the fluid streams flow through the chamber 140, the components in the fluid streams are separated depending on interactions with the fluid processing medium used in the chamber 140. After passing through the chamber 140, the distributed fluid streams flow through the fractal plates 205 of the fractal collector 150 of the first fractal cell 120 and exit the first fractal cell 120 as a single processed fluid stream. The fluid stream is similarly processed in parallel through a second and subsequent fractal cell(s) 120 such that a single processed fluid stream exits each of the second and subsequent fractal cells 120 of the fractal flow devices 100, 100', 100", 100'". The processed fluid stream of each fractal cell 120 is combined into a product stream in which the desired component is separated from other components of the fluid stream.

By utilizing fractal packs 110 in the fractal flow devices 100, 100', 100", 100'", increased capacity, reduced footprint, reduced pressure increases, and increased flow rates may be achieved. The capacity of the fractal flow devices 100, 100', 100", 100'" according to the embodiments hereof may be tailored as desired by increasing or decreasing the number of fractal cells 120 in each fractal pack 110 and/or by increasing or decreasing the number of fractal packs 110 in the fractal flow devices 100, 100', 100", 100'". Since the fractal packs 110 include multiple fractal cells 120 positioned adjacent to one another, each of which includes the fractal distributor 130, chamber 140, and fractal collector 150, the fractal pack 110 may be easily modified to achieve the desired capacity by including more or fewer fractal cells 120 depending on the intended application. By utilizing such a modular design, the fractal packs 110 provide increased capacity to the fractal flow devices 100, 100', 100", 100''' without having to increase the diameter of the fractal plates 205 or other components of the fractal flow devices 100, 100', 100", 100'''. Thus, the necessity of redesigning the fractal flow devices 100, 100', 100", 100''' for every desired change in capacity is avoided and the fractal flow devices 100, 100', 100", 100''' may be easily expanded in an economical fashion.

The footprint of the fractal flow devices 100, 100', 100", 100''' according to embodiments hereof may also be maintained at substantially the same size because the capacity of the fractal flow devices 100, 100', 100", 100''' can be increased or decreased simply by adding or removing, respectively, fractal packs 110 or fractal cells 120. Thus, increasing the capacity of the fractal flow devices 100, 100', 100", 100''' does not increase the overall size of the fractal flow devices 100, 100', 100", 100''' as is needed with conventional equipment. Since the increased processing capacity is provided by the additional fractal cells 120 and/or fractal packs 110, the same processing area is provided in a volume that occupies a small footprint and the fractal cells 120 and/or fractal packs 110 provide a flexible and efficient use of space. Also, no additional mechanical support for the fractal flow devices 100, 100', 100", 100''' is needed because the size and weight of the fractal plates 205 or other components of the fractal flow devices 100, 100', 100", 100''' are not increased as the desired capacity increases. In contrast, when additional capacity is needed with conventional equipment, the conventional equipment must be redesigned by increasing the diameter of the plates, which increases pressures within the conventional equipment, increases the footprint of the conventional equipment, and increases the size and weight of the conventional equipment.

By utilizing the fractal packs 110, pressure increases in the fractal flow devices 100, 100', 100", 100''' are also reduced or eliminated because the diameter of the fractal plates 205 or other components of the fractal flow devices 100, 100', 100", 100''' does not need to be correspondingly increased. Increased flow rates of the fluid stream through the fractal pack 110 are also possible relative to the flow rate through conventional equipment due to the large decrease in linear velocity of the fluid stream and large decrease in pressure drop across the chamber 140. In addition, fluid channeling and turbulence, which are common problems with conventional equipment as flow rates increase, are not observed with the fractal flow devices 100, 100', 100", 100''' according to the embodiments hereof.

After being apprised of the instant disclosure, one of ordinary skill in the art will be readily able to make and use the invention.

While the disclosure is susceptible to various modifications and alternative forms, specific embodiments have been shown by way of example in the drawings and have been described in detail herein. However, the disclosure is not intended to be limited to the particular forms disclosed. Rather, the disclosure is to cover all modifications, equivalents, and alternatives falling within the scope hereof as defined by the following appended claims and their legal equivalents.

What is claimed is:

1. A fractal flow device, comprising:
   at least one fractal pack, the at least one fractal pack comprising:
   at least two fractal cells, each fractal cell comprising a fractal distributor, a chamber adjacent the fractal distributor and comprising a fluid processing medium, and a fractal collector adjacent the chamber, a fractal distributor of one fractal cell of the at least two fractal cells maintained in direct contact with at least one fractal collector of another fractal cell of the at least two fractal cells by one or more fastening elements, and the at least two fractal cells comprising shoulders configured to position the at least two fractal cells in a horizontal direction on a support structure.

2. The fractal flow device of claim 1, wherein the fractal distributor, the chamber, and the fractal collector are in fluid communication with one another.

3. The fractal flow device of claim 1, wherein each of the fractal distributor and the fractal collector comprises a fractal pattern.

4. The fractal flow device of claim 1, wherein the at least two fractal cells are positioned horizontally adjacent to one another.

5. The fractal flow device of claim 1, wherein the at least two fractal cells are positioned vertically adjacent to one another.

6. The fractal flow device of claim 1, wherein each of the fractal distributor and the fractal collector comprises at least one fractal plate comprising a fractal pattern.

7. The fractal flow device of claim 6, wherein the fractal patterns of the fractal distributor and the fractal collector are the same.

8. The fractal flow device of claim 6, wherein the fractal patterns of the fractal distributor and the fractal collector are different.

9. The fractal flow device of claim 6, wherein the fractal distributor and the fractal collector comprise the same number of fractal plates.

10. The fractal flow device of claim 6, wherein the at least one fractal plate of the fractal distributor or of the fractal collector comprises at least one fractal plate inlet, at least one fractal plate outlet, and at least one channel in fluid communication with the at least one fractal plate inlet and the at least one fractal plate outlet.

11. The fractal flow device of claim 10, wherein the fractal distributor comprises an outlet density of greater than approximately 64 outlets/ft$^2$.

12. The fractal flow device of claim 6, wherein the fractal distributor comprises three fractal plates, a first fractal plate of the three fractal plates comprising one fractal plate inlet and four fractal plate outlets, a second fractal plate of the three fractal plates comprising four fractal plate inlets and sixteen fractal plate outlets, and a third fractal plate of the three fractal plates comprising sixteen fractal plate inlets and two hundred fifty six fractal plate outlets.

13. The fractal flow device of claim 6, wherein the fractal collector comprises three fractal plates, a first fractal plate of the three fractal plates comprising two hundred fifty six fractal plate inlets and sixteen fractal plate outlets, a second fractal plate of the three fractal plates comprising sixteen fractal plate inlets and four fractal plate outlets, and a third fractal plate of the three fractal plates comprising four fractal plate inlets and one fractal plate outlet.

14. The fractal flow device of claim 1, wherein the fluid processing medium comprises an ion exchange resin.

15. The fractal flow device of claim 1, wherein the at least one fractal pack is configured for series operation, parallel operation, primary/secondary series operation, simulated moving bed operation, or carousel-type fluid operation.

16. The fractal flow device of claim 1, wherein the one or more fastening elements secure the at least two fractal cells of the at least one fractal pack.

17. The fractal flow device of claim 1, wherein the one or more fastening elements are selected from the group consisting of end plates, a support head, a hydraulic press, a hydraulic jack, and bolts.

18. A method of using a fractal flow device, comprising:
introducing a fluid stream to a fractal flow device, the fluid stream comprising multiple components and the fractal flow device comprising at least one fractal pack, the at least one fractal pack comprising:
at least two fractal cells, each fractal cell comprising a fractal distributor, a chamber adjacent the fractal distributor and comprising a fluid processing medium, and a fractal collector adjacent the chamber, and a fractal distributor of one fractal cell of the at least two fractal cells maintained in direct contact with at least one fractal collector of another fractal cell of the at least two fractal cells by one or more fastening elements, and the at least two fractal cells comprising shoulders configured to position the at least two fractal cells in a horizontal direction on a support structure:
flowing the fluid stream through the at least one fractal pack; and
separating at least one component from the fluid stream to produce a product stream.

19. The method of claim 18, wherein flowing the fluid stream through the at least one fractal pack comprises flowing the fluid stream through the at least two fractal cells in parallel.

20. The method of claim 18, wherein flowing the fluid stream through the at least one fractal pack comprises flowing the fluid stream through at least two fractal packs in series.

21. The method of claim 18, wherein flowing the fluid stream through the at least one fractal pack comprises flowing the fluid stream through a fractal predistributor comprising connector element.

22. The method of claim 18, wherein flowing the fluid stream through the at least one fractal pack comprises uniformly distributing the fluid stream through a chamber containing a bed of fluid processing medium.

23. The fractal flow device of claim 1, wherein the one or more fastening elements are selected from the group consisting of one or more end plates, one or more support heads, one or more hydraulic presses, one or more hydraulic jacks, one or more bolts, and a combination thereof.

24. The fractal flow device of claim 1, wherein the one or more fastening elements are only positioned at opposing ends of the at least one fractal pack.

25. The fractal flow device of claim 1, wherein the fractal flow device comprises two or more fractal packs and the two or more fractal packs are configured in series.

26. The fractal flow device of claim 1, wherein the fractal flow device comprises two or more fractal packs and the two or more fractal packs are configured in parallel.

27. The fractal flow device of claim 1, further comprising a connector element external to the at least one fractal pack.

28. The fractal flow device of claim 1, further comprising a connector element internal to the at least one fractal pack.

29. The method of claim 18, wherein flowing the fluid stream through the at least one fractal pack comprises flowing the fluid stream in a vertical direction through the at least one fractal pack.

30. The method of claim 18, wherein flowing the fluid stream through the at least one fractal pack comprises flowing the fluid stream in a horizontal direction through the at least one fractal pack.

* * * * *

UNITED STATES PATENT AND TRADEMARK OFFICE
CERTIFICATE OF CORRECTION

| | |
|---|---|
| PATENT NO. | : 10,561,965 B2 |
| APPLICATION NO. | : 15/176919 |
| DATED | : February 18, 2020 |
| INVENTOR(S) | : Vadim N. Kochergin and Michael M. Kearney |

Page 1 of 1

It is certified that error appears in the above-identified patent and that said Letters Patent is hereby corrected as shown below:

In the Specification
    Column 9,     Line 59,     change "valve 605″, and" to --valve 605‴, and--

In the Claims
    Claim 18,     Column 13,     Line 24,     change "support structure:" to --support structure;--

Signed and Sealed this
Seventh Day of April, 2020

Andrei Iancu
*Director of the United States Patent and Trademark Office*